United States Patent [19]

Gross et al.

[11] Patent Number: 5,416,594
[45] Date of Patent: May 16, 1995

[54] SURFACE SCANNER WITH THIN FILM GAUGE

[75] Inventors: Kenneth P. Gross, San Carlos; George J. Kren, Los Altos Hills; Christopher F. Bevis, San Francisco, all of Calif.

[73] Assignee: Tencor Instruments, Mountain View, Calif.

[21] Appl. No.: 95,144

[22] Filed: Jul. 20, 1993

[51] Int. Cl.⁶ .............................................. G01N 21/88
[52] U.S. Cl. ..................................... 356/237; 356/382
[58] Field of Search ................................. 356/382, 237

[56] References Cited

U.S. PATENT DOCUMENTS

| | | | |
|---|---|---|---|
| 4,531,838 | 7/1985 | Sawamura | 356/382 |
| 4,601,576 | 7/1986 | Galbraith | 356/237 |
| 4,720,191 | 1/1988 | Siegel et al. | 356/237 |
| 4,740,708 | 4/1988 | Batchelder | 356/237 |
| 4,865,445 | 9/1989 | Kurigama et al. | 356/382 |
| 4,902,131 | 2/1990 | Yamazaki et al. | 356/237 |
| 5,076,692 | 12/1991 | Neukermans et al. | 356/538 |
| 5,125,741 | 6/1992 | Okada et al. | 356/237 |
| 5,189,481 | 2/1993 | Jann et al. | 356/73 |

FOREIGN PATENT DOCUMENTS 193041  8/1988  Japan ..................... 356/237

*Primary Examiner*—Richard A. Rosenberger
*Attorney, Agent, or Firm*—Schneck & McHugh

[57] ABSTRACT

An optical surface scanner for semiconductor wafers and like substrates having one channel with a detector receiving collected scattered light and another channel with a detector receiving reflected light. The scattered light signal is indicative of surface haze, particle count and size, while the reflected light signals are indicative of film thickness and/or surface properties as in the case of an opaque or absorbing layer. The latter signal may be used to correct the particle count and size determination and may also be used simultaneously for thin film measurement. The reflectivity or thin film measurement signals may be used to characterize a film layer controller to improve the accuracy of the deposited thickness of the layer.

24 Claims, 4 Drawing Sheets

SURFACE SCANNER WITH THIN FILM GAUGE

DESCRIPTION

1. Technical Field

The present invention relates to an optical method and apparatus for quality control measurements in the manufacture of semiconductor wafers and the like.

2. Background Art

To control the quality of integrated circuits, semiconductor wafers or other substrates are inspected for defects by optically scanning the surface with apparatus similar to that described in U.S. Pat. No. 4,601,576 to L. K. Galbraith ("Galbraith scanner"). Wafers have a mirror-like surface which is reflective of light, but optical scanners such as the Galbraith scanner rely upon scattering of light from particles and defects for inspection purposes. In Galbraith scanners, there are two types of optical signals, the desired scattered light signals and an undesired specularly reflected light signal which must be suppressed. The scattered light signals are derived from both particle scattering and from diffuse surface scattering known as "haze". The specularly reflected signal is the incident beam minus the components which are lost by scattering and absorption at the surface. In the past, an exit aperture in the light collection optics or a beam dump has been provided for input beam termination in order to rid the scattered light collection system of the undesired reflected beam signal.

In other surface scanners using light scattering from a beam, the directly reflected beam has been used to complement the scattered light signal for diverse measurements. In U.S. Pat. No. 5,189,481, P. C. Jann et al. use the specularly reflected beam to determine local slope of a wafer to ascertain surface profile. In U.S. Pat. No. 5,076,692, A. Neukermans et al. use the specularly reflected beam to measure a diffraction pattern from a wafer surface.

In the initial stages of wafer processing, thin metallic and/or dielectric films, such as transparent oxide or nitride layers, are deposited over the surface. Typically, such thin films have a thickness of between 50 angstroms and several tens of microns. It is important to know, for example, oxide thickness over the surface for several reasons. Uniformity of an oxide layer may be desired so that semiconductor devices employing the oxide layers will have uniform properties. The oxide layers are insulative and the electrical performance of semiconductor devices, such as transistors, rely upon an insulative layer of a particular thickness. The deposition of thin layers tends to degrade particle measurement information. Thin layers of oxide or nitride may attenuate the illuminating radiation fields which may be scattered from particles, and in the case of a transparent film which has a thickness of one-quarter of the wavelength of light, the strength of the radiation field at or near the surface is substantially reduced resulting in little or no light scattering for micron-sized defects lying on the surface. Knowledge of film thickness would be useful for compensating this condition or avoiding a measurement at this thickness.

Analogously, for a variety of metal films, such as aluminum or tungsten, knowledge of the reflectivity of the metallic layer, as well as surface scattering, can yield substantial information about the quality and uniformity of the film deposition. Furthermore, similar to the case for transparent dielectrics, a reflectivity map of the surface can be used to enhance detection and yield a more accurate particle size distribution count, since particle scattering strengths are strongly influenced by the surface optical parameters, such as reflectivity. Thus, it may be seen that knowledge of thin film thickness and reflectivity are important both for construction of semiconductor devices and for measurement of defects.

An object of the invention was to devise an instrument which simultaneously measures particle size and count, surface haze and thin film parameters such as reflectivity and thickness.

SUMMARY OF THE INVENTION

The above object has been achieved with a method and apparatus for wafer measurement which consists of a Galbraith type surface scanner similar to that described in U.S. Pat. No. 5,083,035 to J. Pecen et al., assigned to the assignee of the present invention. Rather than dumping or discarding the specular reflected beam, a separate optical sub-system is used to direct the entire scanned reflected beam into a light detector which is configured to measure the reflected light intensity, thus generating a raster scan and reflectivity map for the complete surface. Polarized components of the same beam or a separate laser at a different wavelength, such as a semiconductor laser, may be used to measure the reflectivity at a common point or scan line on the surface, thus yielding a calculated value for film thickness, assuming the optical properties of the film and substrate are known.

Film thickness data for the entire surface is then continuously generated from the raster scan of the reflectivity at the primary wavelength. For multiple transparent films, if the thicknesses and properties for the underlying layers are known, then the overall reflectivity can be measured and hence thickness of the top layer can be computed in an analogous manner. If only one wavelength is used for the primary scanner, preliminary knowledge of the approximate film thicknesses is necessary. Two wavelengths obviate the need for a priori knowledge of approximate thickness of one film layer because data from two measurements at two wavelengths allows a calculation of absolute thickness. Alternatively, a single wavelength measurement may be compared with a priori calibration measurement using a substrate of the same reflectivity as the test substrate and a film of similar optical properties whose thickness is known. Apart from measuring thickness in quantitative terms, the uniformity of thickness across a substrate may be measured by plotting reflectivity across a substrate, such as a wafer, as a quality control step, without a numerical thickness determination. A reflectivity plot or map, alone, is useful as a process control tool to aid in the uniform deposition and manufacture of the thin film process. For the case of opaque absorbing films such as metals, film thickness is not the important parameter to be measured, but absolute surface reflectivity measurements over the wafer surface will yield a map of film uniformity. The use of at least two different wavelengths will allow absolute film thickness determination of the uppermost translucent layer, assuming the properties of the underlying substrate or other layers are known. In addition, knowledge of the polarization properties of the reflected beam will allow determination of the ellipsometric parameters, thus reducing any possible ambiguity in film thickness determination, particularly near maximum or minimum values. Simultaneously, scattered light information pertaining to light-point-defects and to surface scatter, haze, are collected in separate data collection channels, all data channels being recorded for known positions of the scanning beam. The reflectivity maps are complementary to the surface haze maps and the reflectivity data may be used to correct for particle sizing nonuniformities resulting from film thickness and/or surface roughness variations. The maps are visually displayed. Process controllers may be subsequently adjusted using measurement data.

BEST MODE FOR CARRYING OUT THE INVENTION

Figure 1:
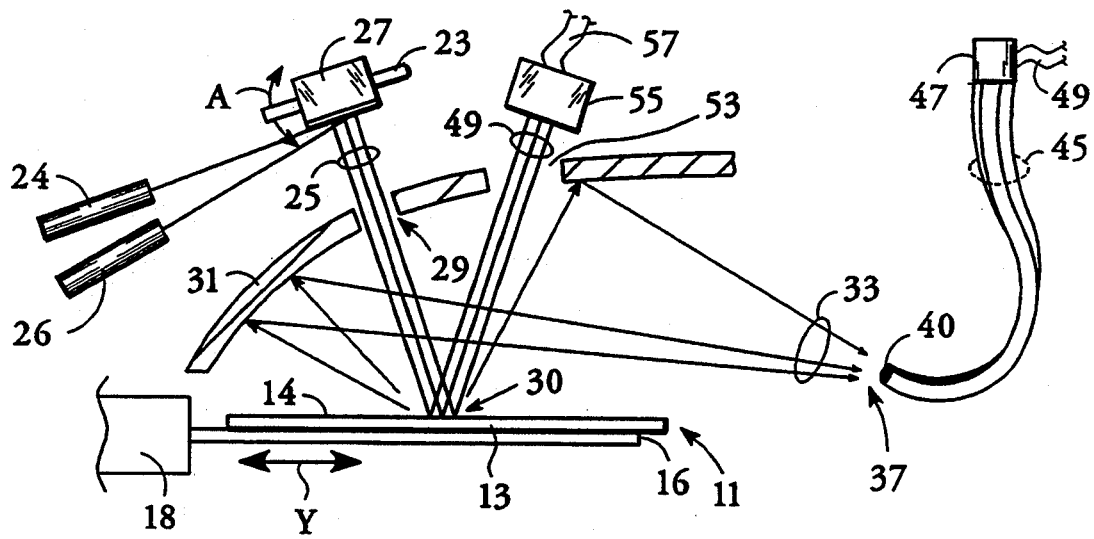
FIG. 1 is a simplified plan view of optical components of a surface scanner with thin film gauge in accord with the present invention.

With reference to FIG. 1, a first embodiment of a particle detector and thickness gauge of the present invention includes a support 11 for a wafer 13. Although a wafer is mentioned as the target object, other coated surfaces, such as reflective glass, or composite materials, or other surface may be an object for testing and measurement by the present invention. The surface 14 of wafer 13 is to be tested for particles, surface haze, reflectivity and film thickness where applicable. Support 11 includes a robotic gripper 16, known as a puck, which is moved by a robot arm 18. The puck is a stiff wafer chuck using a vacuum to keep the wafer in place. The arm 18 moves the wafer in a direction indicated by arrow Y. The position of the support is known and carefully controlled by a motor which reports its position to a computer as discussed below. The particular form of transport is not important so long as the wafer position is known and movable in at least one direction.

A single wavelength laser 24 and optionally a second laser 26, or alternatively a multi-wavelength laser 24 produce a beam 25 which is reflected from scanning mirror 27 toward surface 14. The mirror 27 oscillates in a direction indicated by arrows A about axis 23 under the influence of a galvanometer motor.

Although a second laser 36 is depicted for scanning surface 14 via mirror 27, the second laser 36 could be statically directed to one or more common points on surface 14 to allow a dual wavelength measurement for at least one spatially defined location on the surface to be tested.

Beam 25 is directed through an aperture 29 in the light collector 31 and impinges upon surface 14 in a spot 30. The beam diameter at the point of impingement is typically less than 100 microns. On the other hand, particles of interest are usually on the order of a micron or less. Most larger size particles have been previously removed from the wafer by cleaning. However, since wafers may contain lines or features which are in the order of a micron or less, particles of similar size impact upon the quality of resulting circuits. For this reason, it is important to know the distribution of such particles over a wafer. Sometimes a manufacturing process can be adjusted to take into account particle locations. If the process cannot take the locations into account, at least the locations can be stored in memory so that those circuits which are manufactured in such areas may be designated with a low expectation for reliability.

The beam which impinges upon the wafer has a fraction of its light removed by scattering from particles within the area of impingement. Such light impinges upon light collector 31, an elliptical cylinder and is directed toward a focal line at location 37. An elliptical cylinder has two foci. One focal line is the scanning line where the beam 25 impinges on the target surface at locations such as beam spot 30. The other focal line is at the input 40 of an array of optical fibers 45 arranged in a bundle. One of the properties of an elliptical cylinder is that light originating at one focal line will be directed by the elliptical cylinder to the other focal line. Such elliptical cylinders have been used in Galbraith scanners.

Scattered light enters the fibers 45 at input 40 and is transmitted by the fiber bundle to a scattered light detector 47. The detector 47, which may be a silicon detector or a vacuum-photomultiplier tube, produces an electrical signal representing scattered light intensity which is transmitted from the detector along wires 49.

The specularly reflected beam 49 exits the light collection system through an aperture 53 and impinges upon a detector 55, having a length sufficient to collect light along an entire scanned line. A linear detector or a CCD detector array may be used. Generally, addressable detector elements are not needed because the beam position is known and hence the area being illuminated by the beam is known. Optical detector 55 converts the reflected light signal to an electrical signal which is transmitted as an output on lines 57.

Figure 2:
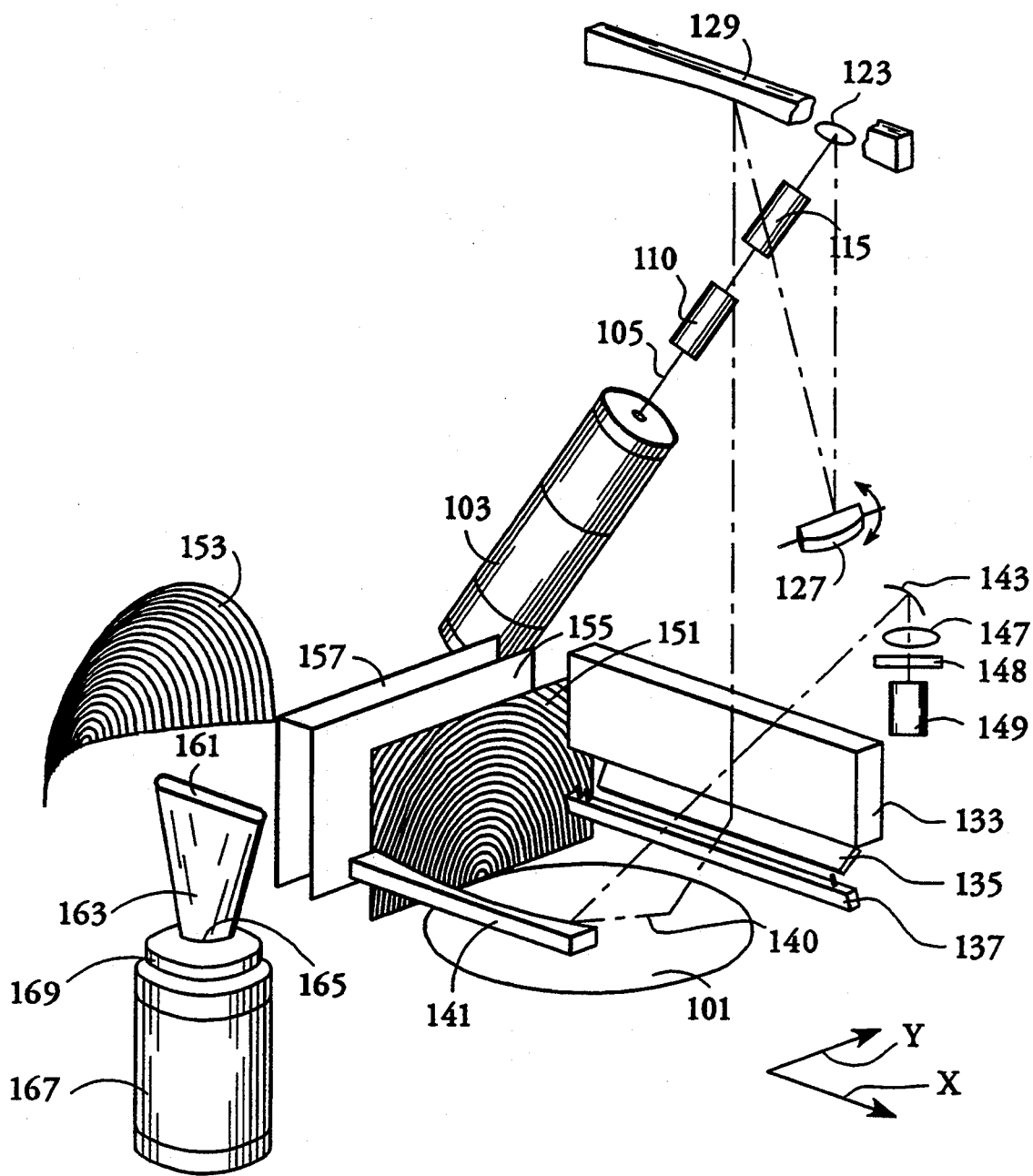
FIG. 2 is a perspective plan view of a preferred embodiment of a surface scanner with thin film gauge in accord with the present invention.

In the preferred embodiment of FIG. 2, laser light from laser 103 is a beam 105 incident upon a wafer 101, at a relatively steep angle of incidence approximately 70–80 degrees in order to reduce background scatter collected from the substrates under test. Rather than collecting forward or backscattered radiation, the scattered light collection system of FIG. 2 collects side scattered light as described below. Laser 103 is a high power, short wavelength radiation source, such as an Argon or HeCd gas laser having an output power of 30 milliwatts or greater which directs beam 105 toward a beam folding mirror 123. The beam first passes through an optical polarizer module 110 containing several polarizing elements used to establish the desired polarization state of the illuminating beam.

The polarizing elements are selectable, with motors or actuators which rotate or translate the optical elements into or within the illuminating beam to create the desired polarization state. Three different input polarizations are provided, P-polarization aligned parallel to the plane of incidence; S-polarization aligned perpendicular to the plane of incidence; and circular polarization which is characterized by continuously varying incident polarization, alternating between S-polarization and P-polarization, at the frequency of the light wave.

The appropriately polarized beam is then expanded and spatially filtered with suitable optics 115, and directed to a high precision low-inertia resonant scanner mirror 127 via the beam folding mirror 123. The scanned fan, from scanner mirror 127 is directed to a telecentric scan mirror 129. Such telecentric scan mirrors are described in U.S. Pat. No. 5,168,386 to L. Galbraith.

Scanner 127 which is supported by crossed flexures and driven by an induction torque driver, sweeps the beam across mirror 129 causing a reflected beam to be telecentrically directed through optional beam shaping optics 133 and then to a plane mirror 135 which directs the beam to the substrate 101 at the previously specified angle of incidence. Before impinging upon the substrate the beam passes bar 137 which supports a number of accurately spaced-apart marker pins for establishing the position of the beam. A procedure whereby fixed locations of marker pins are used to establish beam location is described in U.S. Pat. No. 5,083,035 to J. Pecen et al. The beam scans across the width of the wafer, perpendicular to within one milliradian to the wafer's line of advance indicated by the arrow.

The wafer is moved by a robotic puck, shown in FIG. 1 but not shown in FIG. 2. The position of the scan line is intended to be kept in the same linear path. The combination of beam scanning in the X direction and wafer motion in the Y direction, perpendicular to the X direction, provides full raster scanning of the wafer.

Figure 3:
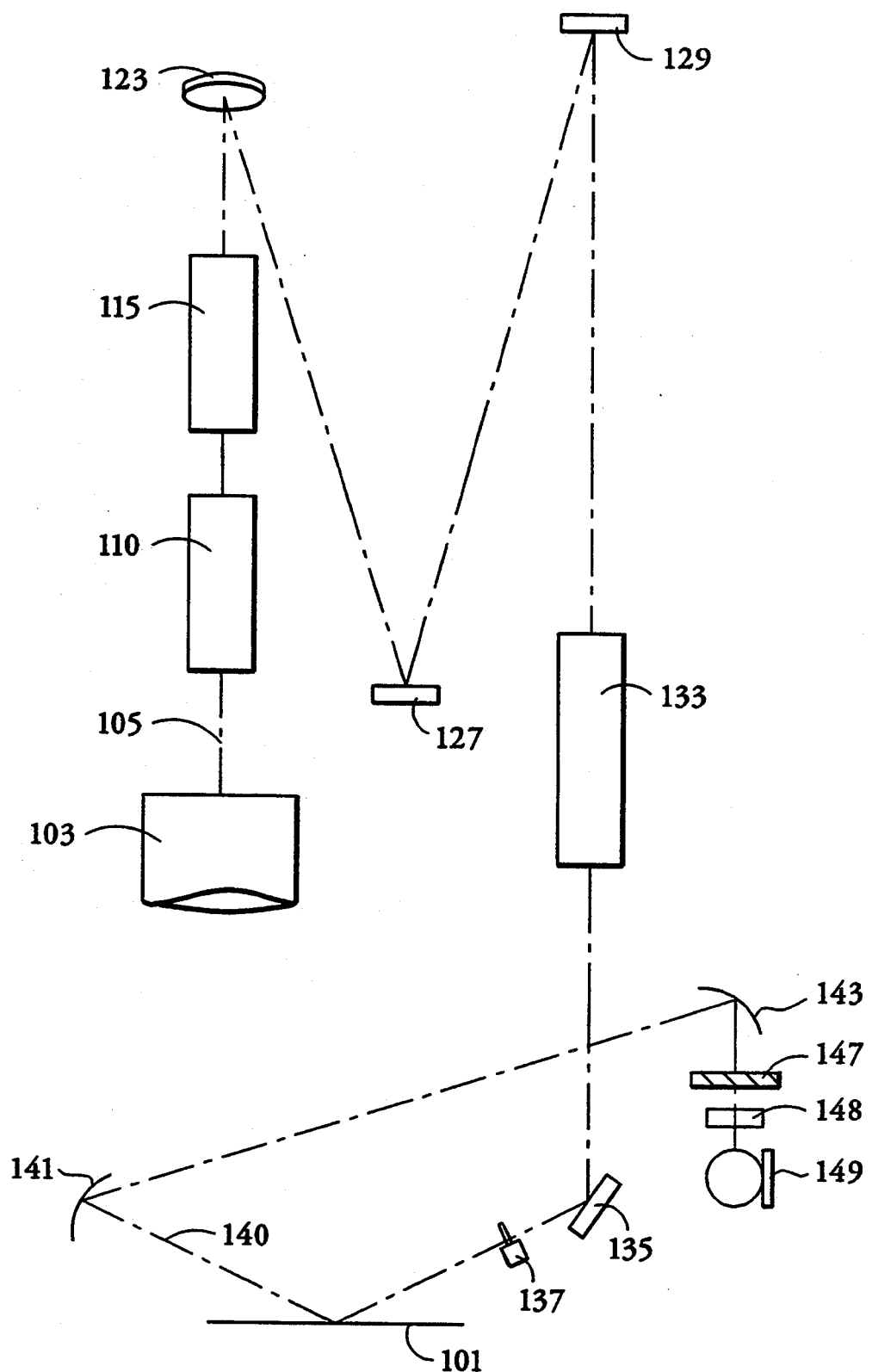
FIG. 3 is a simplified side view of the apparatus of FIG. 2, illustrating the illumination and reflection elements.
Figure 4:
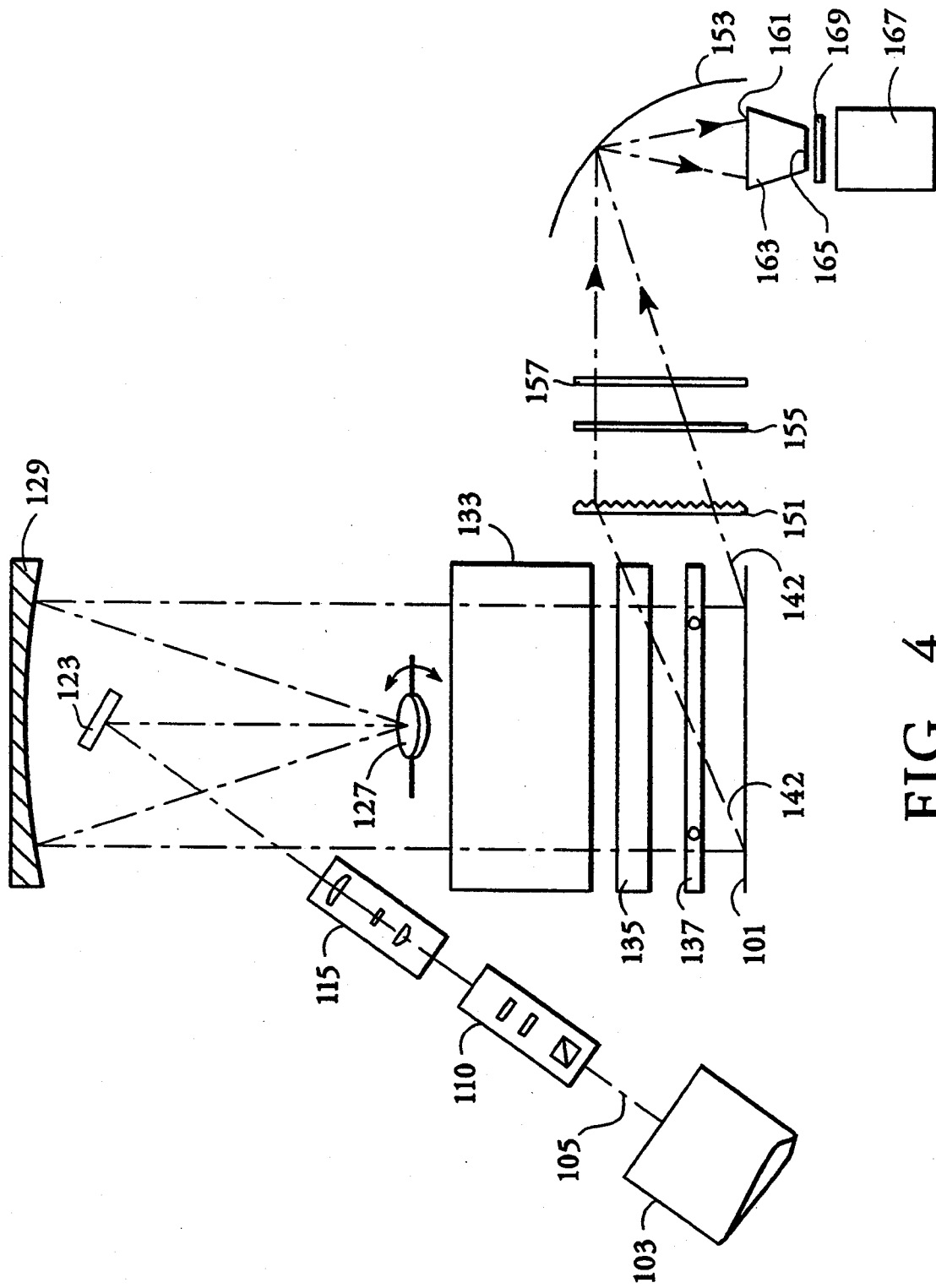
FIG. 4 is another simplified view of the apparatus of FIG. 2, at right angles to FIG. 3, illustrating the illumination and scattered light collector elements.

There are two components to the beam after incidence on the wafer, a reflected component and a scattered component, as depicted in FIGS. 3 and 4, as well as FIG. 2. The first beam component 140, a specular component illustrated in FIG. 3, is reflected from wafer 101 to a set of reflectivity mirrors 141, 143 which direct the entire scanned beam into an integrating sphere or equivalent detector module 149 for radiometric measurement of the reflected power. The first mirror 141 is designed to capture the zero order specular beam plus some fraction of semi-specular power at larger angles. The full included angle for the reflectivity measurement is about 15 degrees. Polarization optics 148, consisting of a polarizer, or a retarder, or a modulator, or a combination of the above, placed in front of detector module 149 would allow measurements of the polarization state of the reflected beam and the determination of the ellipsometric angles, $\Psi$, $\Delta$, of the reflector. These ellipsometric parameters which characterize the relative amplitudes of the reflection coefficients for the P- and S-polarizations and their phase shift difference are well known, prior art being widespread in the literature. An attenuator 147 placed before the polarizers and detector chamber ensures that the enclosure used for beam termination has very low light leakage thereby also serving the purpose of a light trap.

The second component of the beam which was incident on the wafer is a diffusely scattered component 142 illustrated in FIG. 4. This component can be collected from a variety of locations either parallel or transverse to the plane of incidence. Most commonly a 90 degree side scatter geometry is employed using a relatively high numerical aperture collection lens 151, often chosen to be of the Fresnel type. Light from this component is directed toward a reflective mirror 153 and through polarizing elements 155 and 157. Polarizers 155 and 157 allow selection of one of three collection polarization states. These filters can be configured to pass the S-polarization, the P-polarization or both. The optimum polarization configuration for the detection of particles and surface features such as haze and/or scratches, depends on the physical properties of the substrate, the number and physical properties of any thin films present, as well as surface characteristics and the topography of interfaces.

By using a Fresnel lens of short focal length 151, space may be saved to allow close placement of the polarizer elements. The polarizer elements serve to filter unwanted background light, thereby increasing signal-to-noise ratios for the signals of interest. The mirror 153 directs light to a focal zone in a non-imaging manner, toward the entrance port 161 of an internally diffuse reflecting light section converter 163. Light entering the input port 161 may enter at a wide variety of angles and the diffusely reflective interior surface of the section converter 163 reflects light toward a round output aperture 165 which is joined to a photomultiplier tube 167 having an input aperture of similar dimensions. The section converter 163 makes light impinging on the sensitive portion of the photo-multiplier tube diffuse in order to distribute light over a large area of the detector surface by randomizing incoming rays.

In order to protect the photodetector and to extend the dynamic range of the instrument to include various types of substrates and films, an optical attenuator 169 is placed in front of the sensitive element of the photomultiplier tube when high scattering substrates are being inspected.

In operation, background scatter known as haze, and reflectivity are measured simultaneously during scans of the wafer prior to a particle measurement scan. In the situation where there is a single video display, data from alternate sweeps may be time multiplexed to produce two-dimensional maps of surface haze and surface reflectivity. Haze data must be calibrated to the geometry of the collector, using a known standard, such as a 100% white diffuse Lambertian reflector. Reflectivity of the wafer can be measured for all three incident polarization states, namely S, P, and circular. The polarization state, and hence ellipsometric parameters of the reflected beam are also measured by employing polarization analyzers 148. Reflectivity is calibrated into absolute reflectances by means of a standard material such as silicon, or silicon with a single oxide layer of known thickness. When the reflectivity detector is not being used for reflectivity measurements, the reflectivity sub-system serves as a beam dump.

Figure 5:
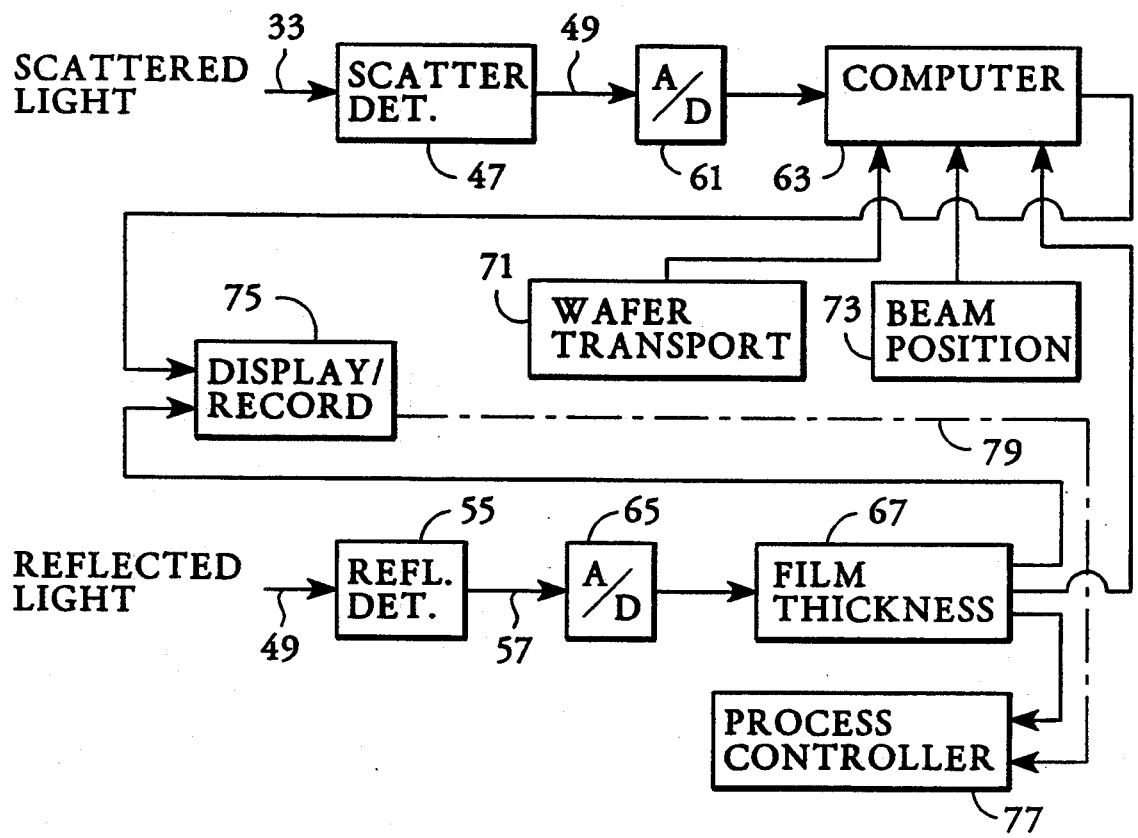
FIG. 5 is a block diagram of electrical components of a surface scanner with thin film gauge in accord with the present invention.

In FIG. 5, scattered light 33 is seen to impinge on the scattering detector 47 which has an electrical signal output 49. The electrical signal from the scattering detector is fed to an analog-to-digital converter 61 which serves as an input to computer 63, similar to a type 386 or 486 computer. A second input signal for the computer is derived from reflected light 49 which impinges upon the detector 55 having an electrical signal output on line 57. This output is fed to an analog-to-digital converter 65 which addresses a film thickness calculator or lookup table 67. The film thickness calculator is programmed with a standard film thickness formula based upon the intensity and ellipsometric parameters of the reflected light signal. Such a calculator may be part of computer 63 but is shown as a separate block because a different function is performed. Formulas for computing thin film thickness using discrete wavelengths are well known in the prior art pertaining to the field of reflection ellipsometry. Once the thin film determination is made, a signal representing the thin film thickness is transmitted to computer 63. The computer then can adjust particle size measurements based upon the intensity of scattered light from scattering detector 47.

The film may diminish particle size by attenuating the scattered light signal from the particles. This effect is dependent upon the size of the particles and the thickness of the film. Calibration tests establish the amount of attenuation versus thickness and these results are stored in the computer for establishing true sizing and counting.

The computer 63 also receives a signal from the wafer transport 71 indicating the wafer position along the Y-axis. The beam position is derived from an angle encoder 73 measuring the position of a scanning mirror. As the mirror oscillates back and forth, beam position signals are generated by the encoder 73 which reports beam position along an X-axis to computer 63. An alternative method of measuring beam position is described in U.S. Pat. No. 5,083,035 to J. Pecen et al., assigned to the assignee of the present invention. Once computer 63 contains the X,Y address of the beam on a wafer, a plot of particles, resembling a star map may be made. Such a particle map is shown in U.S. Pat. No. 4,766,324 to S. Saadat et al. The computer may also be used to perform statistical calculations on particle size, placing particles of different size ranges in bins so that particle size distributions will be known. The previously described particle map may be displayed on a visual display 75 and recorded in a recorder associated with the display, such as a hard drive.

Quantitative film thickness measurements where applicable, can be used to characterize and correct the deposition parameters of a film layer controller. It may also be recognized that reflectivity measurements and/or a qualitative or relative film thickness determination, are also quite useful for correcting particle count and size measurements as well, and for providing information on the quality or uniformity of any surface or thin film, transparent or opaque.

We claim:

1. An apparatus for surface inspection comprising,
    a focused scanning beam illuminating a spot on a specularly reflective wafer having a film layer and light scattering elements thereon,
    means for providing relative motion between the beam and the wafer,
    a first detector positioned to intercept scattered light from said light scattering elements and producing an electrical signal representing scattering,
    a second detector positioned to intercept specularly reflected light from said film layer and producing an electrical signal representing reflectivity of the film layer in response to said specularly reflected light,
    means for logging the position of the beam on the wafer during scanning,
    means for determining, at said spot, the thickness of said film, using detected reflected light, and the presence of scattering elements, using detected scattered light, said determining means including means for producing a first electrical signal from light received by the first detector, and means for producing a second electrical signal from light received by the second detector,
    means for mapping the signals representing light scattering and reflectivity as a function of the position of the beam, and
    means for adjusting scattered light information carried by the first electrical signal using the second electrical signal.

2. The apparatus of claim 1 wherein said spot is scanned over the entire surface of the wafer.

3. Optical apparatus for inspection of reflective articles comprising,
    means for directing a focused scanning beam onto a reflective surface having a film coating thereon, the beam impinging on the surface at a spot,
    means for directing light reflected from said spot to a first detector,
    means for directing light scattered from said spot to a second detector,
    means for simultaneously determining, at said spot, the thickness of said film, using detected reflected light, and the presence of scattering elements, using detected scattered light, said determining means including means for producing a first electrical signal from light received by the first detector, representing reflected light, and means for producing a second electrical signal from light received by the second detector, representing scattered light information, and
    means for adjusting scattered light information carried by the second electrical signal using the first electrical signal.

4. The apparatus of claim 3 wherein said means for directing a scanning beam onto a reflective surface comprises beam polarizing means for producing S, P and circular beam polarizations.

5. The apparatus of claim 3 wherein said means for directing a scanning beam onto a reflective surface comprises a telecentric optical member.

6. The apparatus of claim 3 wherein said means for collecting light scattered from said surface comprises a Fresnel lens and a reflective focussing optical member.

7. The apparatus of claim 3 wherein said means for collecting light scattered from said surface comprises a reflective focussing optical member and a longitudinal slit in a light randomizer interposed between the reflective member and a light sensitive input area of the second detector.

8. The apparatus of claim 7 wherein said light randomizer comprises a tube having opposed ends with said longitudinal slit at one end and an opposite end matching in area the input area of the second detector.

9. The apparatus of claim 3 wherein said means for directing light reflected from said surface to a first detector is at an angle greater than thirty degrees to said means for collecting light scattered from said surface to a second detector.

10. The apparatus of claim 3 wherein a reflective article to be inspected is mounted on a robotic arm for motion in at least one direction.

11. The apparatus of claim 3 wherein said means for directing a scanning beam onto said reflective surface to be inspected comprises first and second lasers having different wavelengths.

12. A method of inspecting substrates having thin film coatings comprising,
    directing a focused beam of light toward a substrate having a film coating, the beam impinging on the substrate at a spot,
    measuring light scattered from said substrate, at said spot, with a first detector,
    measuring light reflected from said substrate, at said spot, with a second detector, determining, at said spot, the thickness of said film coating, using the measured reflected light, and the presence of scattering elements, using the measured scattered light, producing a first electrical signal from light received by the first detector, producing a second electrical signal from light received by the second detector, adjusting scattered light information carried by the first electrical signal using the second electrical signal, and determining the uniformity of said film coating using the measured reflected light from a plurality of spots.

13. The method of claim 12 wherein the determining of uniformity of said film coating comprises using the measured reflected light in comparison with previously measured values.

14. The method of claim 12 wherein the determining of uniformity of said film coating comprises determining the thickness of said film coating where said coating is transparent.

15. The method of claim 12 further defined by correcting the measurement of said light scattered from the substrate based upon the measurement of reflected light.

16. The method of claim 12 further defined by making said scattered and reflected light measurement at the same location.

17. The method of claim 16 further defined by repeatedly making said measurements at a plurality of locations on a wafer.

18. The method of claim 12 further defined by visually displaying scattered light and film thickness measurements on a map of said substrate.

19. The method of claim 12 further defined wherein said beam of light has a single wavelength.

20. The method of claim 12 wherein said beam of light has more than one wavelength.

21. The method of claim 12 further defined by displaying a map of film topography based on said uniformity determination.

22. The method of claim 21 further defined by displaying a map of light scattering elements on the substrate.

23. The method of claim 12 further defined by displaying a single map of film topography based on said uniformity determination and light scattering elements on the substrate.

24. The method of claim 12 further defined by subsequently adjusting a film deposition process based upon said determinations.

* * * * *